United States Patent
Mukai et al.

(10) Patent No.: US 11,083,681 B2
(45) Date of Patent: *Aug. 10, 2021

(54) HAIR COSMETIC COMPOSITION, HAIR COLORING AGENT COMPOSITION, AND HAIR COLOR TREATMENT METHOD

(71) Applicant: SUNNYPLACE CO., LTD., Tokyo (JP)

(72) Inventors: Nobuhito Mukai, Tokyo (JP); Takashi Mukai, Tokyo (JP)

(73) Assignee: SUNNYPLACE CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/630,691

(22) PCT Filed: Dec. 19, 2017

(86) PCT No.: PCT/JP2017/045450
§ 371 (c)(1),
(2) Date: Jan. 13, 2020

(87) PCT Pub. No.: WO2019/016977
PCT Pub. Date: Jan. 24, 2019

(65) Prior Publication Data
US 2021/0085586 A1     Mar. 25, 2021

(30) Foreign Application Priority Data

Jul. 19, 2017  (JP) .............................. JP2017-140408
Jul. 19, 2017  (JP) .............................. JP2017-140409
Jul. 19, 2017  (JP) .............................. JP2017-140412

(51) Int. Cl.
*A61Q 5/10* (2006.01)
*A61K 8/49* (2006.01)
(Continued)

(52) U.S. Cl.
CPC .............. *A61K 8/4946* (2013.01); *A61K 8/19* (2013.01); *A61K 8/20* (2013.01); *A61K 8/22* (2013.01);
(Continued)

(58) Field of Classification Search
CPC .............. A61Q 5/10; A61K 2800/4324; A61K 2800/884; A61K 8/342; A61K 2800/48;
(Continued)

(56) References Cited

U.S. PATENT DOCUMENTS

2016/0128915 A1\* 5/2016 Konno ................... B65D 83/62
424/62

FOREIGN PATENT DOCUMENTS

| JP | H4-342518 | 11/1992 |
| JP | H04-342518 | 11/1992 |

(Continued)

OTHER PUBLICATIONS

English translation of the Japanese Patent No. JP2012171952 A (dated Jan. 27, 2021).\*

(Continued)

*Primary Examiner* — Eisa B Elhilo
(74) *Attorney, Agent, or Firm* — ALG Intellectual Property, LLC

(57) ABSTRACT

A hair cosmetic that has a better color when performing hair dye includes a hair cosmetic composition containing an alkali agent, an amino acid, a higher alcohol having 12 to 22 carbon atoms, a surfactant, and a thickener. The alkaline agent may be at least one of aqueous ammonia, ammonium carbonate, sodium carbonate, ethanolamines, ammonium bicarbonate, and arginine.

6 Claims, 1 Drawing Sheet

(51) Int. Cl.
*A61K 8/19* (2006.01)
*A61K 8/20* (2006.01)
*A61K 8/22* (2006.01)
*A61K 8/24* (2006.01)
*A61K 8/34* (2006.01)
*A61K 8/36* (2006.01)
*A61K 8/362* (2006.01)
*A61K 8/365* (2006.01)
*A61K 8/41* (2006.01)
*A61K 8/44* (2006.01)
*A61K 8/60* (2006.01)
*A61K 8/73* (2006.01)
*A61K 8/92* (2006.01)
*A61K 8/98* (2006.01)

(52) U.S. Cl.
CPC ............... *A61K 8/24* (2013.01); *A61K 8/34* (2013.01); *A61K 8/342* (2013.01); *A61K 8/345* (2013.01); *A61K 8/361* (2013.01); *A61K 8/362* (2013.01); *A61K 8/365* (2013.01); *A61K 8/41* (2013.01); *A61K 8/416* (2013.01); *A61K 8/44* (2013.01); *A61K 8/447* (2013.01); *A61K 8/602* (2013.01); *A61K 8/731* (2013.01); *A61K 8/922* (2013.01); *A61K 8/987* (2013.01); *A61Q 5/10* (2013.01); *A61K 2800/48* (2013.01)

(58) Field of Classification Search
CPC ............... A61K 2800/432; A61K 8/92; A61K 2800/5426; A61K 2800/594

USPC ..................................................... 8/405, 426
See application file for complete search history.

(56) References Cited

FOREIGN PATENT DOCUMENTS

| | | |
|---|---|---|
| JP | H11-501947 | 2/1999 |
| JP | 2002-114653 | 4/2002 |
| JP | 2002-193761 | 7/2002 |
| JP | 2004-189745 | 7/2004 |
| JP | 2007-314498 | 12/2007 |
| JP | 2008-143829 | 6/2008 |
| JP | 2012-246229 | 12/2012 |
| JP | 2015-040193 | 3/2015 |
| JP | 2017-088502 | 5/2017 |

OTHER PUBLICATIONS

Search Report and Written Opinion received in International Application No. PCT/JP2017/045450; dated Feb. 6, 2018.
Office Action received in corresponding application JP2017-140408 pending before the Japanese Patent Office; dated Apr. 20, 2021.
Office Action received in corresponding application JP2017-140409 pending before the Japanese Patent Office; dated Apr. 20, 2021.
Office Action received in corresponding application JP2017-140412 pending before the Japanese Patent Office; dated Apr. 20, 2021.

* cited by examiner

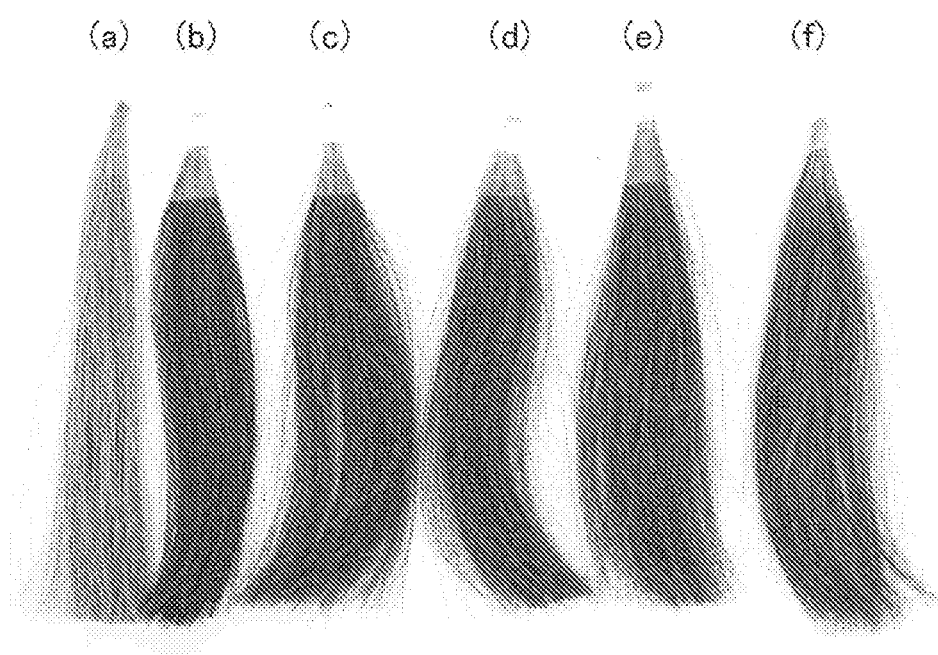

HAIR COSMETIC COMPOSITION, HAIR COLORING AGENT COMPOSITION, AND HAIR COLOR TREATMENT METHOD

TECHNICAL FIELD

The present invention relates to a hair cosmetic composition and a hair cosmetic containing the hair cosmetic composition, and in particular, relates to a hair cosmetic composition and a hair cosmetic containing the hair cosmetic composition capable of reducing skin damage, and having a property of keeping color quality and penetrating dyeing power (Firmly dyes even sideburns that are difficult to dye).

In addition, the present invention also relates to a hair coloring agent composition, and more particularly to a hair coloring agent composition that can reduce skin damage.

In addition, the present invention relates to a hair color treatment method using a hair cosmetic composition and a hair coloring agent composition, and in particular, relates to a hair color treatment method using a hair cosmetic composition and a hair coloring agent composition capable of reducing skin damage, and having a property of keeping color quality and penetrating dyeing power (Firmly dyes even sideburns that are difficult to dye).

BACKGROUND ART

As hair coloring, there are mainly hair color, which is a permanent hair dye for quasi drugs, and hair manicure and hair color treatment, which are semi-permanent hair dyes for cosmetics. In particular, the hair colors of permanent hair dyes containing paraphenylene diamine (oxidative dye) is mainstream, but in the case of black-based dark colors, since the amount of diamine-based compounds increases. More attention is required.

For example, as a hair coloring composition comprising paraphenylenediamine (oxidative dye), a hair coloring composition characterized by comprising (a) a water-soluble peroxygen bleach; (b) a bleaching aid selected from an organic peroxyacid bleach precursor and/or a preformed organic peroxyacid; and (c) one or more hair coloring agents is known (Patent literature 1).

PRIOR ART LITERATURE

Patent Literature

Patent literature 1; JP-A1-H11-501947

DISCLOSURE OF THE INVENTION

Problems to be Resolved by the Invention

However, in the prior art including the above-mentioned Patent literature 1, those containing paraphenylene diamine (oxidative dye) have a larger amount of diamine based compound in the case of a dark black color as described above, so further attention is required. In addition to this, in recent years, skin disorders have been reported due to the use of a substance called paraphenylenediamine (oxidative dye).

In addition, the hair manicure of semi-permanent hair dye is characterized in that the color (acidic dye) penetrates into the inside of hair after a single use and the hair manicure has a feature of a color lasting for 2 to 3 weeks. However, the longer it is left on the scalp, the more difficult it is to remove the dye. Moreover, it is difficult for practitioner to apply to the edge of the hairline. Therefore, such hair dye tends to be avoided in salons and beauty salons because the operator's specific skill is needed and the dyeing is worse than the hair color.

On the other hand, in the above-mentioned hair color, it is possible to dye even cortex (hair cortex. inside hair), but in hair color treatment, since it is aimed that the cuticle (hair skin) and cortex near the hair surface are dyed, in some cases, there was problem that it was not possible to achieve a hair color that has a sufficient property of keeping color quality.

Therefore, the hair cosmetic composition of the present invention aims to provide a hair cosmetic composition and a hair cosmetic that have a better property of keeping color quality when performing hair dye.

Another object of the hair coloring agent composition of the present invention is to provide a hair coloring agent that is free of paraphenylenediamine and can reduce skin damage.

In addition, the hair color treatment method of the present invention is to provide a hair color treatment method that has a better property of keeping color quality in performing hair dyes, is free of paraphenylenediamine, and can reduce skin damage.

Means of Solving the Problems

In order to achieve the above object, the present inventors have intensively studied the treatment before and after the hair color treatment, and as a result, have found the hair cosmetic composition of the present invention.

That is, the hair cosmetic composition of the present invention is characterized by comprising an alkali agent, an amino acid, a higher alcohols having 12 to 22 carbon atoms, a surfactant, and a thickener.

Further, in a preferred embodiment of the hair cosmetic composition of the present invention, it is characterized in that the alkaline agent is at least one selected from ammonia water, ammonium carbonate, sodium carbonate, ethanolamines, ammonium bicarbonate, and arginine.

Further, in a preferred embodiment of the hair cosmetic composition of the present invention, it is characterized in that the ethanolamines is monoethanolamine, diethanolamine, or triethanolamine.

Further, in a preferred embodiment of the hair cosmetic composition of the present invention, it is characterized in that the amino acid is at least one selected from cysteine, arginine, lysine, or histidine.

Further, in a preferred embodiment of the hair cosmetic composition of the present invention, the hair cosmetic composition is characterized by being applied to hair before hair color treatment.

Further, the hair cosmetic of the present invention is characterized by including the hair cosmetic composition of the present invention.

Further, in order to achieve the above object, the present inventors have intensively studied hair color treatments, and as a result, have found the hair coloring agent composition of the present invention.

That is, the hair coloring agent composition of the present invention is characterized by comprising a basic dye, an HC dye, an amino acid, a cationic surfactant, a thickener, an oil agent, a pH adjuster, and a wetting agent, wherein the hair coloring agent composition has a pH of 6.8 or more.

Further, in a preferred embodiment of the hair coloring agent composition of the present invention, the pH adjuster is characterized by being at least one selected from citric acid, phosphoric acid, lactic acid, malic acid, aqueous ammonia, ammonium hydrogen carbonate, ammonium carbonate, potassium hydroxide, sodium hydroxide, monoethanolamine, ammonium phosphate, sodium citrate, ammonium citrate, sodium lactate, potassium phosphate, and sodium phosphate.

Further, in a preferred embodiment of the hair coloring agent composition of the present invention, the amino acid is characterized by being at least one selected from cysteine, arginine, lysine, or histidine.

Further, in a preferred embodiment of the hair coloring agent composition of the present invention, the basic dye is characterized by being at least one selected from Basic Blue 3, Basic Blue 7, Basic Blue 99, Basic Red 76, Basic Yellow 57, Basic Brown 16, or Basic Brown 17, in the name of (INCI (INCI: International Nomenclature of Cosmetic Ingredient).

Further, in a preferred embodiment of the hair coloring agent composition of the present invention, the HC dye is characterized by being at least one selected from HC Blue 2, HC Yellow 2, HC Yellow 4, HC yellow 5, HC red 1, HC red 3, or HC orange 1, in the name of INCI (INCI: International Nomenclature of Cosmetic Ingredient).

Further, in a preferred embodiment of the hair coloring agent composition of the present invention, the cationic surfactant is characterized by being a quaternary ammonium salt and/or a tertiary amine.

Further, in a preferred embodiment of the hair coloring agent composition of the present invention, the quaternary ammonium salt is characterized by being an alkyltrimethylammonium chloride solution, stearyltrimethylammonium chloride, or stearyltrimethylammonium bromide.

Further, in a preferred embodiment of the hair coloring agent composition of the present invention, the tertiary amine is characterized by being stearic acid dimethylaminopropylamide, stearic acid diethylaminoethylamide, or behenamidopropyldimethylamine.

Further, a hair coloring agent of the present invention is characterized in that the hair coloring agent comprises the hair coloring agent composition according to the present invention.

In addition, in order to achieve the above object, the present inventors have intensively studied the hair color treatment method, and as a result, have found the hair color treatment method of the present invention.

That is, a hair color treatment method is characterized by comprising a step of applying a hair cosmetic comprising an alkaline agent, a first amino acid, a higher alcohol having 12 to 22 carbon atoms, a surfactant, and a thickener; and a step of applying a hair coloring agent comprising a basic dye, an HC dye, a second amino acid, a first cationic surfactant, a thickener, an oil agent, a first pH adjusting agent, and a wetting agent, wherein the hair coloring agent has a pH of 6.8 or more.

Further, in a preferred embodiment of the hair color treatment method of the present invention, the method is characterized by further comprising a step of applying a cuticle tightening agent including at least one selected from sodium bromate and hydrogen peroxide, a second cationic surfactant, and a second pH adjusting agent, after applying the hair coloring agent.

Further, in a preferred embodiment of the hair color treatment method of the present invention, the method is characterized in that when the hair cosmetic is applied, an exposure time is 5 to 20 minutes.

Further, in a preferred embodiment of the hair color treatment method of the present invention, the method is characterized in that when the hair coloring agent is applied, an exposure time is 1 to 10 minutes using a hair dryer and then left for 5 to 15 minutes.

Further, in a preferred embodiment of the hair color treatment method of the present invention, the method is characterized in that the alkaline agent is at least one selected from ammonia water, ammonium carbonate, sodium carbonate, ethanolamines, ammonium hydrogen carbonate, and arginine.

Further, in a preferred embodiment of the hair color treatment method of the present invention, the method is characterized in that the first or second amino acid is at least one selected from cysteine, arginine, lysine, or histidine.

Further, in a preferred embodiment of the hair color treatment method of the present invention, the method is characterized by further comprising a step of applying a shampoo agent Effect of Invention According to the hair cosmetic composition of the present invention, the hair coloring agent composition of the present invention, and the hair color treatment method of the present invention, there are advantage effects it is possible to provide a hair color product that it does not contain paraphenylenediamine, and therefore, is suitable for peoples who suffer from rashes or who are concerned about contact dermatitis, and also is suitable for peoples who are aged persons and have a possibility of using hair color for a long time due to aging. Therefore, according to the hair cosmetic composition of the present invention, the hair coloring agent composition of the present invention, and the hair color treatment method of the present invention, there are advantage effects it is possible to provide a hair color product that can be used with peace of mind and keep a good color tone (having a property of keeping color quality) and can be applied safely even up to the newborn part (newborn organization of skin) without worrying about adhesion to the scalp even on the practitioner side of treatment.

BRIEF DESCRIPTION OF THE DRAWINGS

FIG. 1 is a diagram showing the degree of color fading state when a hair coloring agent according to an embodiment of the present invention is applied. As the hair bundle, 50% (product number: BM2-M-50) (15 cm×2 g) of black and white hair manufactured by Beaulax Co., Ltd. was used. It is shown that FIG. 1 (a) is an untreated hair bundle, (b) is the hair bundle of 1 time of hair washing, (c) is 5 times of hair washing, (d) is 10 times of hair washing, (e) is 20 times of hair washing, and (0 is 30 times of hair washing, respectively.

MODE FOR CARRYING OUT THE INVENTION

The hair cosmetic composition of the present invention is characterized by comprising an alkali agent, an amino acid, higher alcohols having 12 to 22 carbon atoms, a surfactant, and a thickener. In the hair cosmetic composition (basic cuticle swelling agent) of the present invention, the alkaline agent contained in the hair cosmetic can open the cuticle. In other words, in hair color treatments and the like, the cuticle (cuticle of the root sheath, or hair skin) and cortex near the hair surface are dyed, and there are cases where a hair color with sufficiently good color cannot be achieved. However, if the hair cosmetic composition of the present invention is applied, it is possible to open the cuticle, and as a result, it has an advantageous effect that a hair color which has a property of keeping color quality can be achieved.

That is, although basic dyes and HC dyes originally dye cuticles and cortex close to the surface, by using the hair cosmetic composition (swelling agent) of the present invention, the present inventors have found that it is possible to dye with dyes and HC dyes, even if it is a deeper part of the hair.

The amount of the alkaline agent is not particularly limited, but from the viewpoint that the cuticle can be efficiently opened and the swelling effect can be satisfactorily exhibited the pH value of the hair cosmetic composition of the present invention can be preferably 7.0 to 11.5, more preferably, the pH can be adjusted to 8.5 to 11.5, and still more preferably pH 9.0 to 9.7. The amount of the alkaline agent is not particularly limited, but it can be preferably 1 to 3% by mass with respect to the total amount of the composition from the viewpoint of efficiently opening the cuticle and exhibiting a good swelling effect.

In addition, the amount of the amino acid is not particularly limited, but from the viewpoint of keeping the moisture and flexibility of the hair, it can be preferably 0.01 to 0.5% by mass, more preferably 0.01 to 0.3%, still more preferably 0.02 to 0.2 mass %, with respect to the total amount of the composition.

In the hair cosmetic composition of the present invention, the higher alcohol having 12 to 22 carbon atoms is not particularly limited, but from the viewpoint of imparting smoothness to the hair, improving emulsification stability, and adjusting the viscosity, mention may be made of cetyl alcohol, lauryl alcohol, myristyl alcohol, cetostearyl alcohol, stearyl alcohol, and behenyl alcohol etc.

Further, the amount of the higher alcohols having 12 to 22 carbon atoms is not particularly limited, but from the viewpoint of imparting smoothness to hair, improving emulsification stability and adjusting the viscosity, it can be preferably 0.1 to 5.0% by mass, more preferably 0.1 to 3.0% by mass, and still more preferably 0.2 to 2.0% by mass, with respect to the total amount of the composition.

In a preferred embodiment of the hair cosmetic composition of the present invention, the alkaline agent is not particularly limited, but for example, mention may be made of at least one selected from ammonia water, ammonium carbonate, sodium carbonate, ethanolamines, ammonium hydrogen carbonate, and arginine. In addition, in a preferred embodiment of the hair cosmetic composition of the present invention, the ethanolamines are characterized by being monoethanolamine, diethanolamine, and/or triethanolamine. Ethanolamines such as monoethanolamine are non-volatile and have little odor, but they remain highly on the hair and may hurt the hair. In addition, arginine has a high affinity with hair, but the action thereof as an alkaline agent is weak and the reaction is mild. Ammonia water has a pungent odor due to its volatility, but has a feature that it has little residue on hair and reacts quickly. From this point of view, as the alkaline agent mention may be made of preferably ammonia water.

In a preferred embodiment of the hair cosmetic composition of the present invention, the amino acid can include at least one selected from cysteine, arginine, lysine, and/or histidine. Although it has been reported that arginine or histidine in the hair decrease with aging, in the present invention, arginine, histidine hydrochloride, and lysine hydrochloride blended in the hair cosmetic composition (swelling agent) of the present invention can penetrate into the hair and exhibit a hair repair effect.

The hair cosmetic composition of the present invention can contain a surfactant and a thickener. About these surfactant and a thickener, unless it deviates from the effect of this invention, it does not specifically limit, a well-known thing can be used.

Further, in a preferred embodiment of the hair cosmetic composition of the present invention, the hair cosmetic composition is characterized by being applied to hair before hair color treatment. That is, in the hair cosmetic composition (basic cuticle swelling agent) of the present invention, the alkaline agent contained in the hair cosmetic composition can open the cuticle. In other words, in hair color treatments and the like, the cuticle (hair skin) and cortex near the hair surface are dyed, and there are cases where a hair color with sufficiently good color cannot be achieved. However, if the hair cosmetic composition of the present invention is applied, it is possible to open the cuticle, and as a result, it has an advantageous effect that a hair color which has a property of keeping color quality can be achieved. This effect can be more exerted by applying the hair treatment agent of the present invention before the hair color treatment.

Moreover, in order to tighten the cuticle after applying the hair cosmetic composition of the present invention and performing hair color treatment, for example, it is also possible to apply a cutie tightening agent containing sodium bromate.

In addition, the hair cosmetic of the present invention is characterized by including the above-described hair cosmetic composition of the present invention.

Next, an example of the hair coloring agent composition of the present invention will be described as follows.

The hair coloring agent composition of the present invention is characterized by comprising a basic dye, an HC dye, an amino acid, a cationic surfactant, a thickener, an oil agent, a pH adjuster, and a wetting agent, wherein the hair coloring agent composition has a pH of 6.8 or more. In the hair color composition of the present invention, it was found that the cuticle can be easily opened by adjusting the pH to 6.8 or more, and at the same time, basic amino acids such as L-arginine, L-lysine, L-histidine, and salts thereof can be fed into the hair. As a result, it was found that this product can be used for color treatment while the basic amino acid that has flowed out of the pain can be supplied and repaired. That is, in hair color treatments and the like, the cuticle (hair skin) and cortex near the hair surface are dyed, and there are cases where a hair color with sufficiently good color cannot be achieved. However, if the hair coloring agent composition of the present invention is applied, it is possible to open the cuticle, and as a result, it has an advantageous effect that a hair color which has a property of keeping color quality can be achieved.

Further, in a preferred embodiment of the hair coloring agent composition of the present invention, from the viewpoint of easy opening of the cuticle and adjusting pH to 6.8 or more, as the pH adjusting agent mention may be made of at least one selected from citric acid, phosphoric acid, lactic acid, malic acid, ammonia water, ammonium hydrogencarbonate, ammonium carbonate, potassium hydroxide, sodium hydroxide, monoethanolamine, ammonium phosphate, sodium citrate, ammonium citrate, sodium lactate, potassium phosphate, sodium phosphate. From the viewpoint of being weakly alkaline and having little residue on the hair, preferably, as the pH adjuster, mention may be made of ammonium bicarbonate, sodium bicarbonate and the like.

From the viewpoint that the cuticle can be efficiently opened and a property of keeping color quality can be exhibited well, the pH value of the hair coloring agent composition of the present invention can be adjusted to preferably 6.8 or more, more preferably 7.0 to 9.0, still more preferably 7.3 to 8.0.

In addition, in a preferred embodiment of the hair coloring agent composition of the present invention, the amino acid is characterized by being at least one selected from cysteine, arginine, lysine, or histidine. In addition, the amount of the amino acid is not particularly limited, but from the viewpoint of keeping the moisture and flexibility of the hair, it can be set to preferably 0.01 to 0.5% by mass, more preferably 0.01 to 0.3%, still more preferably 0.02 to 0.2 mass %, with respect to the total amount of the composition.

Further, in a preferred embodiment of the hair coloring agent composition of the present invention, the basic dye is characterized by being at least one selected from Basic Blue 3, Basic Blue 7, Basic Blue 99, Basic Red 76, Basic Yellow 57, Basic Brown 16, or Basic Brown 17, in the name of (INCI (INCI: International Nomenclature of Cosmetic Ingredient). Incidentally, INCI (INCI: International Nomenclature of Cosmetic Ingredient) is an international labeling name for cosmetic ingredients prepared by the International Nomenclature Committee (INC). In addition, the amount of the basic dye is not particularly limited, but from the viewpoint that the dyeing power is not strong but damage to the hair is small, it can be preferably 0.0005 to 5% by mass, more preferably 0.01 to 3% by mass, and still more preferably 0.1 to 1% by mass with respect to the total amount of the composition.

Further, in a preferred embodiment of the hair coloring agent composition of the present invention, the HC dye is characterized by being at least one selected from HC Blue 2, HC Yellow 2, HC Yellow 4, HC yellow 5, HC red 1, HC red 3, or HC orange 1, in the name of INCI (INCI: International Nomenclature of Cosmetic Ingredient). Incidentally, INCI (INCI: International Nomenclature of Cosmetic Ingredient) is an international labeling name for cosmetic ingredients prepared by the International Nomenclature Committee (INC). Further, the amount of the HC dye is not particularly limited. However, since the HC dye dyes the hair, from the viewpoint of deeper color development, it can be preferably 0.0005 to 5% by mass, more preferably 0.01 to 3% by mass, and still more preferably 0.1 to 1.5% by mass, with respect to the total amount of the composition.

Further, in a preferred embodiment of the hair coloring agent composition of the present invention, from the viewpoint of further improving the touch given to the hair, the cationic surfactant is characterized by being a quaternary ammonium salt and/or a tertiary amine. In addition, in a preferred embodiment of the hair coloring agent composition of the present invention, the quaternary ammonium salt is characterized by being an alkyltrimethylammonium chloride solution, stearyltrimethylammonium chloride, or stearyltrimethylammonium bromide. Further, in a preferred embodiment of the hair coloring agent composition of the present invention, the tertiary amine is characterized by being stearic acid dimethylaminopropylamide, stearic acid diethylaminoethylamide, or behenamidopropyldimethylamine. Further, the amount of the cationic surfactant is not particularly limited, but from the viewpoint of improving the hair dyeing ability of the basic dye, it can be preferably 0.01 to 10% by mass, more preferably 0.1 to 5% by mass, and still more preferably 1 to 3% by mass, based on the total amount of the composition.

In addition, the hair color composition of the present invention may contain a thickener, a wetting agent, an oil agent and the like. In the present invention, these thickeners and the like are not particularly limited as long as they do not depart from the effects of the present invention, and a known thicker can be used. As the thickener, from the viewpoint of product stability, for example, mention may be made of hydroxyethyl cellulose, xanthan gum, polyethylene glycol and the like. Further, the amount of the thickener is not particularly limited, but from the viewpoint of improving the stability of the product, it can be preferably 0.05 to 0.8% by mass, more preferably 0.1 to 0.5% by mass with, still more preferably, it can be 0.2 to 0.4 mass %, with respect to the total amount of the composition.

Also, as the wetting agent, mention may be made of glycerin, diglycerin, and 1,3-butylene glycol. Further, the amount of the wetting agent is not particularly limited, but from the viewpoint of easy application of the product, it can be preferably 0.1 to 15% by mass, more preferably 0.5 to 10% by mass, still more preferably 1 to 5% by mass, with respect to the total amount of the composition.

Also, as the oil agent, mention may be made of fats and oils, waxes, hydrocarbons, alkyl glyceryl ethers, esters, silicones, higher alcohols, and the like. Further, the amount of the oil agent is not particularly limited, but from the viewpoint of preventing the drying of the coating leaving time and the stability of the product, it can be preferably 1 to 30% by mass, more preferably 2 to 20% by mass, and still more preferably may be 3 to 15% by mass.

Further, the hair coloring agent of the present invention is characterized by including the hair coloring agent composition of the present invention. The hair coloring agent composition of the present invention can be appropriately included in the hair coloring agent as desired or depending on the use of the hair coloring agent.

Next, the hair color treatment method of the present invention will be described as follows.

The hair color treatment method of the present invention is characterized by comprising a step of applying a hair cosmetic comprising an alkaline agent, a first amino acid, a higher alcohol having 12 to 22 carbon atoms, a surfactant, and a thickener, a step of applying the hair coloring agent wherein the hair coloring agent comprises a basic dye; an HC dye; a second amino acid; a first cationic surfactant; a thickener; an oil agent; a first pH adjuster; a wetting agent, and the hair coloring agent has a pH of 6.8 or more.

First, an example of a hair cosmetic composition and a hair cosmetic applicable to the present invention will be described as follows.

The hair cosmetic composition applicable to the present invention is characterized by comprising an alkali agent, an amino acid, higher alcohols having 12 to 22 carbon atoms, a surfactant, and a thickener. In the hair cosmetic composition (basic cuticle swelling agent) of the present invention, the alkaline agent contained in the hair cosmetic can open the cuticle. That is, in hair color treatments and the like, the cuticle (hair skin) and cortex near the hair surface are dyed, and there are cases where a hair color with sufficiently property of keeping a good color cannot be achieved. However, if the hair cosmetic composition of the present invention is applied, it is possible to open the cuticle, and as a result, it has an advantageous effect that a hair color which has a property of keeping color quality can be achieved.

In other words, basic dyes and HC dyes originally dye cuticles and cortex close to the surface, but by using the hair cosmetic composition (swelling agent) of the present invention, the present inventors have found that it is possible to dye with basic dyes and HC dyes up to deeper parts of the hair.

the pH value of the hair cosmetic composition is not particularly limited, but from the viewpoint that the cuticle can be efficiently opened and the swelling effect can be satisfactorily exhibited, the pH value of the hair cosmetic composition of the present invention can be adjusted to preferably 7.0 to 11.5, more preferably pH 8.5 to 11.5, and still more preferably pH 9.0 to 9.7. The amount of the alkali agent is not particularly limited, but from the viewpoint of efficiently opening the cuticle and exhibiting a good swelling effect, it can be preferably 1 to 3% by mass with respect to the total amount of the composition.

Moreover, the amount of the amino acid is not particularly limited, but from the viewpoint of keeping the moisture and flexibility of the hair, it can be set to preferably 0.01 to 0.5% by mass, more preferably 0.01 to 0.3%, and still more preferably 0.02 to 0.2% by mass, with respect to the total amount of the composition.

In the hair cosmetic composition applicable to the present invention, the higher alcohols having 12 to 22 carbon atoms is not particularly limited, but from the viewpoint of imparting smoothness to the hair, improving the emulsion stability, and adjusting the viscosity, mention may be made of cetyl alcohol, lauryl alcohol, myristyl alcohol, cetostearyl alcohol, stearyl alcohol, and behenyl alcohol and the like.

Further, the amount of the higher alcohols having 12 to 22 carbon atoms is not particularly limited, but from the viewpoint of imparting smoothness to hair, improving emulsification stability and adjusting the viscosity, preferably, the content can be 0.1 to 5.0% by mass, more preferably 0.1 to 3.0% by mass, and still more preferably 0.2 to 2.0% by mass.

In a preferred embodiment, the alkaline agent is not particularly limited, and examples thereof can include at least one selected from ammonia water, ammonium carbonate, sodium carbonate, ethanolamines, ammonium bicarbonate, and arginine. In a preferred embodiment of the hair cosmetic composition of the present invention, the ethanolamine is characterized by being monoethanolamine, diethanolamine, and/or triethanolamine. Ethanolamines such as monoethanolamine are non-volatile and have little odor, but they remain highly on the hair and may hurt the hair. Further, arginine has a high affinity with hair, but it is weak regarding an action as an alkaline agent and has a mild reaction. Ammonia water has a pungent odor due to its volatility, but it is characterized by little residue on the hair and quick reaction. From this point of view, as the alkaline agent, mention may be made of preferably ammonia water.

Further, in a preferred embodiment, the amino acid may include at least one selected from cysteine, arginine, lysine, and/or histidine. Although it has been reported that arginine and histidine in the hair decrease with aging, in the present invention, it is possible for arginine, histidine hydrochloride, lysine hydrochloride blended in the hair cosmetic composition (swelling agent) of the present invention to penetrate into the hair and exert a hair repair effect.

The hair cosmetic composition applicable to the present invention may contain a surfactant and a thickener. About these surfactant and a thickener, unless it deviates from the effect of this invention, it does not specifically limit and a well-known one can be used.

Further, in a preferred embodiment, the hair cosmetic composition is characterized in that it is applied to hair before hair color treatment. That is, in the hair cosmetic composition (basic cuticle swelling agent) of the present invention, the alkaline agent contained in the hair cosmetic composition can open the cuticle. That is, in hair color treatments and the like, the cuticle (hair skin) and cortex near the hair surface are dyed, and there are cases where a hair color with sufficiently property of keeping a good color cannot be achieved. However, if the hair cosmetic composition of the present invention is applied, it is possible to open the cuticle, and as a result, it has an advantageous effect that a hair color which has a property of keeping color quality can be achieved. This effect can be more exerted by applying the hair treatment agent of the present invention before the hair color treatment.

In addition, in order to tighten the cuticle after applying the hair cosmetic composition applicable to the present invention and performing hair color treatment, for example, it is also possible to apply a cutie tightening agent including sodium bromate.

Further, a hair cosmetic applicable to the present invention is characterized by including the above-described hair cosmetic composition of the present invention.

Next, the hair coloring agent composition and hair coloring agent applicable to the present invention will be described as follows.

A hair coloring agent composition applicable to the present invention is characterized by comprising a basic dye, an HC dye, an amino acid, a cationic surfactant, a thickener, an oil agent, a pH adjuster, and a wetting agent, wherein the hair coloring agent composition has a pH of 6.8 or more. In the hair coloring agent composition applicable to the present invention, it has been found that the cuticle can be easily opened by setting the pH to 6.8 or more, and at the same time, it has been also found that this product can be used for color treatment capable of sending the basic amino acids such as L-arginine, L-lysine, L-histidine, and salts thereof, etc., into the interior portion of the hair and adding and repairing the basic amino acids that have flowed out due to pain. That is, in hair color treatments and the like, the cuticle (hair skin) and cortex near the hair surface are dyed, and there are cases where a hair color with sufficiently property of keeping a good color cannot be achieved. However, if the hair coloring agent composition of the present invention is applied, it is possible to open the cuticle, and as a result, it has an advantageous effect that a hair color which has a property of keeping color quality can be achieved.

Further, in a preferred embodiment of the hair coloring agent composition applicable to the present invention, from the viewpoint of easy opening of the cuticle and adjusting the pH to 6.8 or more, the pH adjusting agent can be at least one selected from citric acid, phosphoric acid, lactic acid., Malic acid, aqueous ammonia, ammonium bicarbonate, ammonium carbonate, potassium hydroxide, sodium hydroxide, monoethanolamine, ammonium phosphate, sodium citrate, ammonium citrate, sodium lactate, potassium phosphate, sodium phosphate. From the viewpoint of being weakly alkaline and having little residue on the hair, preferably, the pH adjuster can include ammonium bicarbonate, sodium bicarbonate and the like.

From the viewpoint that the cuticle can be efficiently opened and the color tone can be exhibited well, the pH value of the hair coloring agent composition of the present invention can be adjusted to preferably 6.8 or more, more preferably 7.0 to 9.0, and still more preferably 7.3 to 8.0.

Further, in a preferred embodiment of the hair coloring agent composition applicable to the present invention, the amino acid is characterized by being at least one selected from cysteine, arginine, lysine, or histidine. Further, the amount of the amino acid is not particularly limited, but from the viewpoint of keeping the moisture and flexibility of the hair, it can be set to preferably 0.01 to 0.5% by mass, more preferably 0.01 to 0.3% by mass and still more preferably 0.02 to 0.2% by mass with respect to the total amount of the composition.

Moreover, in a preferred embodiment of the hair coloring agent composition applicable to the present invention, the basic dye is characterized by being at least one selected from Basic Blue 3, Basic Blue 7, Basic Blue 99, Basic Red 76, Basic Yellow 57, Basic Brown 16, or Basic Brown 17, in the name of (INCI (INCI: International Nomenclature of Cosmetic Ingredient). Incidentally, INCI (INCI: International Nomenclature of Cosmetic Ingredient) is an international labeling name for cosmetic ingredients prepared by the International Nomenclature Committee (INC). The amount of the basic dye is not particularly limited, but from the viewpoint that the dyeing power is not strong but damage to the hair is small, it can be preferably 0.0005 to 5% by mass, more preferably 0.01 to 3% by mass, and still more preferably 0.1 to 1% by mass, with respect to the total amount of the composition.

Further, in a preferred embodiment of the hair coloring agent composition applicable to the present invention, the HC dye is characterized by being at least one selected from HC Blue 2, HC Yellow 2, HC Yellow 4, HC yellow 5, HC red 1, HC red 3, or HC orange 1, in the name of INCI (INCI: International Nomenclature of Cosmetic Ingredient). Incidentally, INCI (INCI: International Nomenclature of Cosmetic Ingredient) is an international labeling name for cosmetic ingredients prepared by the International Nomenclature Committee (INC). Further, the amount of the HC dye is not particularly limited, but from the viewpoint of exhibiting a deeper color in order to dye the inside of the hair by the use of the HC dye, it can be preferably 0.0005 to 5% by mass, more preferably 0.01 to 3% by mass, and still more preferably 0.1 to 1.5% by mass with respect to the total amount of the composition.

Moreover, in a preferred embodiment of the hair coloring agent composition applicable to the present invention, from the viewpoint of further improving the touch to the hair, the cationic surfactant is characterized by being a quaternary ammonium salt and/or a tertiary amine. Further, in a preferred embodiment of the hair coloring agent composition of the present invention, the quaternary ammonium salt is characterized by being an alkyltrimethylammonium chloride solution, stearyltrimethylammonium chloride, or stearyltrimethylammonium bromide. In a preferred embodiment, the tertiary amine is characterized by being stearic acid dimethylaminopropylamide, stearic acid diethylaminoethylamide, or behenamidopropyldimethylamine. Further, the amount of the cationic surfactant is not particularly limited, but from the viewpoint of improving the hair dyeing ability of the basic dye, it can be preferably 0.01 to 10% by mass, more preferably 0.1 to 5% by mass, and still more preferably 1 to 3% by mass, based on the total amount of the composition.

In addition, the hair coloring agent composition applicable to the present invention may contain a thickener, a wetting agent, an oil agent and the like. In the present invention, these thickeners and the like are not particularly limited as long as they do not depart from the effects of the present invention, and known ones can be used. As examples of the thickener, from the viewpoint of product stability, mention may be made of hydroxyethyl cellulose, xanthan gum, polyethylene glycol and the like. Further, the amount of the thickener is not particularly limited, but from the viewpoint of improving the stability of the product, it can be preferably 0.05 to 0.8% by mass, more preferably 0.1 to 0.5% by mass, and still more preferably 0.2 to 0.4% by mass, with respect to the total amount of the composition.

Also, as examples of the wetting agent, mention may be made of glycerin, diglycerin, and 1,3-butylene glycol. Further, the amount of the wetting agent is not particularly limited, but from the viewpoint of easy application of the product, it can be preferably 0.1 to 15% by mass, more preferably 0.5 to 10% by mass, and still more preferably 1 to 5% by mass, with respect to the total amount of the composition.

In addition, as examples of the oil agent, mention may be made of fats and oils, waxes, hydrocarbons, alkyl glyceryl ethers, esters, silicones, higher alcohols, and the like. Further, the amount of the oil agent is not particularly limited, but from the viewpoint of preventing the drying during the standing time after coating and from the viewpoint of the stability of the product, it can be preferably 1 to 30% by mass, more preferably 2 to 20% by mass, and still more preferably 3 to 15% by mass.

Further, the hair coloring agent applicable to the present invention is characterized by including the above-described hair coloring agent composition applicable to the present invention. If desired or depending on the application of the hair coloring agent, the hair coloring agent can appropriately include a hair coloring agent composition applicable to the present invention.

The above is an explanation of examples of hair cosmetics and hair coloring agents.

Further, in a preferred embodiment of the hair color treatment method of the present invention, the method is characterized by further comprising a step of applying a cuticle tightening agent including at least one selected from sodium bromate and hydrogen peroxide, a second cationic surfactant, and a second pH adjusting agent, after applying the hair coloring agent. As the second pH adjusting agent, an acidic pH adjusting agent can be blended. Further, from the viewpoint of returning to a healthy hair condition (isoelectric band pH 4.5 to 5.5), as pH adjusters, may be made of organic acids such as citric acid, phosphoric acid, phytic acid, lactic acid and malic acid, and acidic amino acids such as glutamic acid and the like.

Further, in a preferred embodiment of the hair color treatment method of the present invention, when the hair cosmetic is applied, from the viewpoint that the cuticle can be efficiently opened and the swelling effect can be exhibited well, the standing time (exposure time) is characterized by being 5 to 20. The standing is preferably left as it is, but may be heated.

Further, in a preferred embodiment of the hair color treatment method of the present invention, when the hair color agent is applied, from the viewpoint of efficiently dyeing hair, the standing time (exposure time) is characterized by being 5 to 15 minutes, after heated for 1 to 10 minutes using a hair dryer.

Further, in a preferred embodiment of the hair color treatment method of the present invention, the alkaline agent is characterized by being at least one selected from ammonia water, ammonium carbonate, sodium carbonate, ethanolamines, ammonium bicarbonate, and arginine. Regarding the alkaline agent, reference may be made to the above descriptions in the hair cosmetics and the like applicable to the present invention as mentioned above.

Further, in a preferred embodiment of the hair color treatment method of the present invention, the first or second amino acid is characterized by being at least one selected from cysteine, arginine, lysine, or histidine. As to the first or second amino acid, reference may be made to the above descriptions in the hair cosmetics and hair coloring agent etc., applicable to the present invention as mentioned above.

Further, in a preferred embodiment of the hair color treatment method of the present invention, the hair color treatment method is characterized in that the method further includes a step of applying a shampoo agent. When applying a shampoo agent to hair, from a viewpoint of removing obstruction factors, such as hairdressing agents and sebum, it is preferable to apply it before the treatment of hair cosmetics. In this case, the pH of the shampoo agent may be pH 8 or more, preferably pH 9 to pH 10.7. In this case, as the shampoo agent, Nanosuppliment cleansing shampoo GA (shampoo agent, manufacturer/seller: SUNNY PLACE CO., LTD.), bright hair painter shampoo (shampoo agent, manufacturer/seller: SUNNY PLACE CO., LTD.) or New D & D First (shampoo agent, seller: SUNNY PLACE CO., LTD.) can be used. Moreover, the formulated ingredients of the shampoo agent, so called "Bright Hair Painter Shampoo" at pH 9.0-10.7 may be water, myristic acid, lauric acid, cocamide DEA, hydroxylated K, EDTA-4Na, PEG-75, cocamidopropyl betaine, hydrolyzed silk, hydrolyzed yeast extract, sage extract, rosemary extract, comfrey extract, carrot extract, maroonnier extract, fennel extract, oleic acid PEG-10, BG, PG, ethanol, sorbitol, methylparaben, fragrance, etc.

Also, when applying a shampoo agent to the hair, from the viewpoint of removing obstructive factors such as hair styling agents and sebum it is preferable to apply it after the treatment of the tightening agent. In this case, the pH of the shampoo agent can be preferably weakly acidic. In this case, preferably, Apurucell Shampoo Premium (Shampoo Agent, manufacturer and distributor: SUNNY PLACE CO., LTD.) can be used as the shampoo agent.

Moreover, an example of the treatment steps of the hair color treatment method of the present invention is as follows.
1) A pre-shampooing is performed. (For the purpose of removing hair conditioner and dirt)
2) The hair cosmetic of the present invention (basic cuticle swelling agent) is applied and leave it to stand. (It has been reported that arginine and histidine in the hair decrease with age are reduced. The alkaline agent in the swelling agent can make the cuticle open, and arginine, histidine hydrochloride, and lysine hydrochloride contained in the swelling agent penetrated to an inside of hair to attain a hair repair effect. In addition, basic dyes and HC dyes originally dye cuticles and cortex near the surface, but by using this swelling agent, it is characterized in that deeper parts can be dyed and covered with basic dyes and HC dyes.). As the alkaline agent, mention may be made of aqueous ammonia, ammonium carbonate, sodium carbonate, triethanolamines such as mono, di and tri ethanolamine, ammonium hydrogen carbonate, arginine, and the like.
3) The hair coloring agent (hair color treatment) of the present invention which does not contain paraphenylenediamine is applied and leave it to stand. The base color of this color treatment is a basic dye and HC dye, which are considered to be safer than oxidative dyes. However, since it was dyed on the hair, the color persistence after the hair dyeing was bad, and there was the fault that it was easy to lose color by repeating shampoo. However, the "basic cuticle swelling agent" not only facilitates penetration of the base color, but also contains no acidic dye, so that it can be characterized in that it can be applied from the new part to the hair tip without worrying about adhesion to the scalp.
4) Exposure time: 10-20 hours (warming or natural leaving)
5) Rinse the hair coloring agent (hair color treatment) thoroughly before shampooing.
6) If there is a feeling caused by rinsing after shampooing, apply a "cuticle tightening agent" formulated with sodium bromate and warm up it to tighten the cuticle and increase the refractive index of the hair to increase the gloss.
7) After towel drying, dry with a hair dryer.

EXAMPLE

As mentioned below, an embodiment of the present invention will be concretely explained in more detail with reference to Examples, but the invention is not intended to be interpreted as being limited to the following Examples.

Examples 1 to 3

Regarding alkaline agents, ammonia water, ammonium carbonate, sodium carbonate, triethanolamines such as mono, di, or triethanolamines, ammonium hydrogen carbonate, arginine, and the like are considered. However, ethanolamines such as monoethanolamine are non-volatile and have little odor, but they remain highly on the hair and may hurt the hair. In addition, arginine has a high affinity with hair, but it is weak as to an action as an alkaline agent and has a mild reaction. Aqueous ammonia is the irritating odor due to volatile, but has a property that it has little residue on the hair and reacts quickly. Accordingly, in this embodiment, as the alkaline agent, as an example of ammonia water, it was tested with different concentrations.

In addition, about 80% of human hair is composed of keratin proteins derived from amino acid, L-cysteine is an amino acid that is also abundant in the hair. Therefore, L-cysteine and its salts were tried for the purpose of keeping the hair moisturized and flexible. Typical basic amino acids include L-arginine, L-lysine and L-histidine, but these are known to flow out when damaged, and there was found that 0.01 to 0.5% by mass of basic amino acids and salts thereof are preferable.

Table 1 shows the components of an example of the hair cosmetic composition in one embodiment of the present invention.

TABLE 1

| | | Examples | | |
|---|---|---|---|---|
| | Components | 1 | 2 | 3 |
| Alkaline agent | 25% Ammonia water | 1.00 | 2.00 | 3.00 |
| Amino acid group | L-Cysteine hydrochloride | 1.00 | 1.00 | 1.00 |
| | L-Arginine | 0.10 | 0.10 | 0.10 |
| | L-Lysine hydrochloride | 0.02 | 0.02 | 0.02 |
| | L-Histidine hydrochloride | 0.02 | 0.02 | 0.02 |
| Higher alcohol | Cetyl alcohol | 1.92 | 1.92 | 1.92 |
| | Lauryl alcohol | 0.24 | 0.24 | 0.24 |
| Common ingredients | Polyoxyethylene oleyl ether | 0.39 | 0.39 | 0.39 |
| | Polyoxyethylene lauryl ether | 0.27 | 0.27 | 0.27 |
| | Sodium lauryl sulfate | 0.18 | 0.18 | 0.18 |
| | Concentrated glycerin | 1.00 | 1.00 | 1.00 |
| | Hydrolyzed silk | 0.50 | 0.50 | 0.50 |
| | Cetyltrimethyl-ammonium chloride | 1.50 | 1.50 | 1.50 |
| | Fragrance | 0.20 | 0.20 | 0.20 |
| | Purified water | Residue | Residue | Residue |
| | Total (% by mass) | 100.00 | 100.00 | 100.00 |
| | pH | 8.72 | 9.60 | 10.38 |

TABLE 2

|  |  | Components | Examples | | |
|---|---|---|---|---|---|
|  |  |  | 1 | 2 | 3 |
| A phase |  | Purified water | Residue | Residue | Residue |
|  | Alkaline agent | 25% Ammonia water | 1.00 | 2.00 | 3.00 |
|  | Amino acid group | L-Cysteine hydrochloride | 1.00 | 1.00 | 1.00 |
|  |  | L-Arginine | 0.10 | 0.10 | 0.10 |
|  |  | L-Lysine hydrochloride | 0.02 | 0.02 | 0.02 |
|  |  | L-Histidine hydrochloride | 0.02 | 0.02 | 0.02 |
| B phase | Common ingredients | Concentrated glycerin | 1.00 | 1.00 | 1.00 |
|  |  | Hydrolyzed silk | 0.50 | 0.50 | 0.50 |
|  |  | Cetyltrimethyl-ammonium chloride | 1.50 | 1.50 | 1.50 |
|  |  | Fragrance | 0.20 | 0.20 | 0.20 |
| C phase | Emulsifying stability and viscosity-imparting ingredients | Cetyl alcohol | 1.92 | 1.92 | 1.92 |
|  |  | Lauryl alcohol | 0.24 | 0.24 | 0.24 |
|  |  | Polyoxyethylene oleyl ether | 0.39 | 0.39 | 0.39 |
|  |  | Polyoxyethylene lauryl ether | 0.27 | 0.27 | 0.27 |
|  |  | Sodium lauryl sulfate | 0.18 | 0.18 | 0.18 |
|  |  | Total (% by mass) | 100.00 | 100.00 | 100.00 |
|  |  | pH | 8.72 | 9.60 | 10.38 |

Table 2 shows an example of a method for preparing a hair cosmetic composition according to an embodiment of the present invention. The preparation method is as follows.
Preparation Method:
1. After confirming the dissolution of the amino acid group in the purified water of Phase A in Table 2, the alkaline agent is mixed uniformly. 2. Next, while stirring the A phase of Table 2, the B phase of Table 2 is added and mixed uniformly. 3. Add Phase C in Table 2 with moderate stirring and stir until uniform.

Moreover, the following models and electrodes were used for pH measurement.
Model of pH meter: F-52 (Horiba, Ltd.)
pH meter electrode: Type 9611 (Horiba, Ltd.)

In addition, Table 3 shows details of each component which is used.

TABLE 3

|  | Components | Abbreviation or Product name | Manufacturer |
|---|---|---|---|
|  | Purified water |  |  |
| Alkaline agent | 25% Ammonia water | Reagent grade 25% Ammonia water | Daiseikakou Co., Ltd. |
| Amino acid group | L-Cysteine hydrochloride | CSKE-200 | Osaka Sasaki Chemical Co., Ltd. |
|  | L-Arginine | L-Arginine | Ajinomoto Co., |
|  | L-Lysine hydrochloride | L-Lysine hydrochloride | Pure Chemical Co., Ltd. |
|  | L-Histidine hydrochloride | L-Histidine hydrochloride | Tomo Chemical Co., Ltd. |
| Common ingredients | Concentrated glycerin | Concentrated glycerin for cosmetic | Sakamoto Pharmaceutical Co., Ltd. |
|  | Hydrolyzed silk | SILK-1000 | Seiwa Kasei Co., |
|  | Cetyltrimethyl-ammonium chloride | kohtamin 60W | Kao Corporation |
|  | Fragrance | — | Kotobuki Fragrance Co., Ltd. |
| Emulsifying stability and viscosity-imparting | Cetyl alcohol | EMACOL VS | Sanei Chemical Co., Ltd. |
|  | Lauryl alcohol |  |  |
|  | Polyoxyethylene oleyl ether |  |  |
|  | Polyoxyethylene lauryl ether |  |  |
|  | Sodium lauryl sulfate |  |  |

From the above results, the higher alcohol preferably has 12 to 22 carbon atoms and can be contained for imparting smoothness to the hair, improving the emulsion stability, and adjusting the viscosity. In addition, 25% aqueous ammonia (ammonia water) is preferably 1 to 3% by mass, but considering the feeling of use and speed of reaction, irritation to the hand, and the burden on the scalp, it was found that 2.0% by mass of 25% aqueous ammonia is optimal.

In addition, actually, pretreatment was performed using the hair cosmetic composition of the present invention. That is, if a hair cosmetic (basic cuticle swelling agent) containing the hair cosmetic composition of the present invention is applied and left before hair color treatment, it was found that the alkaline agent in the swelling agent makes the cuticle open, and arginine, histidine hydrochloride, and lysine hydrochloride blended in the swelling agent permeates into the hair and exhibit a hair repair effect.

Thus, in the present invention, when performing hair dye, compared with conventional hair color and hair manicure, in the conventional method, there are problems that 1) if the hair is damaged by repeated dyeing, the hair strength is reduced and elasticity is lost to thin a hair (In the case of hair color), 2) if the scalp rash occurs, the rash part will stain and be difficult to remove (in the case of hair manicure). However, in the present invention, there is no problem of the above 1) and 2), it was found that hair cosmetics with good penetration and dyeing power can be provided. In other words, in the present invention, it has also been found that safety is provided when used in combination with a hair color in addition to color retention.

Next, examples of the hair coloring agent composition etc., of the present invention will be described below, but the present invention is not construed as being limited to the following examples.

Examples 4-5

With regard to the alkali agent (pH adjusting agent), from the viewpoint of being weakly alkaline and difficult to cause skin irritation, in the example, a test was conducted using ammonium bicarbonate as an example.

In addition, about 80% of human hair is composed of amino acid-derived from keratin proteins, L-cysteine is an amino acid that is also abundant in the hair, and in order to keep the hair moisturized and flexible, L-cysteine and its salts were blended. Typical basic amino acids include L-arginine, L-lysine and L-histidine, but these are known to flow out when damaged, and there was found that 0.01 to 0.5% by mass of basic amino acids and salts thereof are preferable.

Table 4 shows components of an example hair coloring agent composition in one embodiment of the present invention.

TABLE 4

| | Components Display name | Example 4 | Example 5 |
|---|---|---|---|
| Water phase | Water | Residue | Residue |
| | Glycerin | 1.00 | 1.00 |
| | BG | 1.00 | 1.00 |
| | Pentylene glycol | 1.00 | 1.00 |
| | Hydroxyethyl cellulose | 0.25 | 0.25 |
| | Steartrimonium bromide | 1.50 | 1.50 |
| | Isopropanol | 1.00 | 1.00 |
| Oil phase | Myristyl alcohol | 5.00 | 5.00 |
| | Behenyl alcohol | 1.00 | 1.00 |
| | Ethylhexyl palmitate | 2.00 | 2.00 |
| | Cetyl palmitate | 1.00 | 1.00 |
| | Glycol stearate | 2.00 | 2.00 |
| | Shea fat | 1.00 | 1.00 |
| Alkaline agent | Ammonium hydrogen | 0.70 | 1.00 |
| Preservatives and refreshing ingredients | Phenoxyethanol | 0.60 | 0.60 |
| | Menthol | 0.10 | 0.10 |
| | Ethanol | 1.00 | 1.00 |
| Antiinflammatory component | Glycyrrhizic acid 2K | 0.10 | 0.10 |
| Pigment | Basic blue 99 | 0.30 | 0.30 |
| | Basic brown 16 | 0.50 | 0.50 |
| | HC blue 2 | 0.60 | 0.60 |
| | HC yellow 4 | 0.20 | 0.20 |
| | HC yellow 2 | 0.10 | 0.10 |
| Amino acid group | Arginine | 0.10 | 0.10 |
| | Histidine HCl | 0.02 | 0.02 |
| | Lysine HCl | 0.02 | 0.02 |
| | Total (% by mass) | 100.00 | 100.00 |
| | pH | 6.80 | 7.50 |

The preparation method is as follows.
Preparation Method:
1. The aqueous phase (water phase) of Table 4 is warmed to 75-77° C. with stirring.
2. The oil phase in Table 4 is stirred while heating to 77-79° C. to make it uniform.
3. The pigment is added to water phase heated to 75-77° C. to homogenize, the oil phase is add to the mixture to emulsify and stir until uniform.
4. The content is slowly cooled, and when the temperature of the content is 43° C. or lower, the preservative, the refreshing component, the antiinflammatory component, and the amino acid group are added and stirred until uniform, and then cooled to 32° C. or lower.

Moreover, the following models and electrodes were used for pH measurement.
Model of pH meter: F-52 (Horiba, Ltd.)
pH meter electrode: Type 9611 (Horiba, Ltd.)

In addition, Table 5 shows details of each component which is used for the test.

TABLE 5

| | Components Display name | Abbreviation or Product name | Manufacturer |
|---|---|---|---|
| Water phase | Water | | |
| | Glycerin | Concentrated glycerin for cosmetic | Sakamoto Pharmaceutical Co., Ltd. |
| | BG | 1,3-butylene glycol-P | KH Neochem Co., Ltd. |
| | Pentylene glycol | | |
| | Hydroxyethyl cellulose | | |
| | Steartrimonium bromide | Catinal STB-70 | Toho Chemical Industry Co., |
| | Isopropanol | | |

TABLE 5-continued

| | Components Display name | Abbreviation or Product name | Manufacturer |
|---|---|---|---|
| Oil phase | Myristyl alcohol | KALCOL 4098 | Kao Corporation |
| | Behenyl alcohol | Lanette 22 | BASF Japan Co., Ltd. |
| | Ethylhexyl palmitate | Cegesoft C24 | BASF Japan Co., Ltd. |
| | Cetyl palmitate | Cutina CP | BASF Japan Co., Ltd. |
| | Glycol stearate | | |
| | Shea fat | Refined shea butter | Koei Kogyo Co., Ltd. |
| pH adjuster (Alkaline agent) | Ammonium hydrogen carbonate | | |
| Preservatives and refreshing ingredients | Phenoxyethanol | Hisolve EPH | Toho Chemical Industry Co., Ltd. |
| | Menthol | L-Menthol | K. Kobayashi & Co., Ltd. |
| | Ethanol | Dehydrated ethanol | Kenei Pharmaceutical Co., Ltd. |
| Antiinflammatory component | Glycyrrhizic acid 2K | Dipotassium glycyrrhizinate | Maruzen Pharmaceutical Co., Ltd. |
| Pigment | Basic blue 99 | | |
| | Basic brown 16 | | |
| | HC blue 2 | | |
| | HC yellow 4 | | |
| | HC yellow 2 | | |
| Amino acid group | Arginine | L-Arginine | Kyowa Hakko Bio Co., Ltd. |
| | Histidine HCl | L-histidine hydrochloride monohydrate | Wako Pure Chemical Industries, Ltd. |
| | Lysine HCl | L-lysine hydrochloride | Wako Pure Chemical Industries, Ltd. |

In addition, a hair colorant containing the hair colorant composition of the present invention was actually prepared, and a color fading test was performed on the hair bundle. The results are shown in FIG. 1. FIG. 1 is a diagram showing the degree of color fading when a hair coloring agent according to one embodiment of the present invention is applied. As the hair bundle, a ratio of black hair to white hair of 50% (product number: BM2-M-50) (15 cm×2 g) manufactured by Beaulax Co., Ltd., was used. FIG. 1 (a) shows an untreated hair bundle, (b) shows a hair bundle of 1 time of a hair wash, (c) shows a hair bundle of 5 times of a hair wash, (d) shows a hair bundle of 10 times of a hair wash, (e) shows a hair bundle of 20 times of a hair wash, (f) shows a hair bundle of 30 times of a hair wash, respectively. As a result, it was found that the hair coloring agent of the present invention was extremely excellent in color fading.

Conventionally, when a "hair color treatment" that does not contain paraphenylenediamine is applied and left as it is, although, the base color of this color treatment is a basic dye and HC dye, which are considered to be safer than oxidative dyes, since it was dyed on the hair, the color persistence after the hair dyeing was bad, and there was the fault that it was easy to lose color due to repeated shampooing. However, from the above results, it was found that not only the base color easily penetrates but also it can be applied from the new part to the hair tip without worrying about adhesion to the scalp because it does not contain an acidic dye.

Thus, in the present invention, when performing hair dye, compared with conventional hair color and hair manicure, in the conventional method, there are problems that 1) if the hair is damaged by repeated dyeing, the hair strength is reduced and elasticity is lost to thin a hair (In the case of hair color), 2) if the scalp rash occurs, the rash part will stain and be difficult to remove (in the case of hair manicure). However, in the present invention, there is no problem of the above 1) and 2), it was found that hair cosmetics with good penetration and dyeing power can be provided. In other words, in the present invention, it has also been found that safety is provided in addition to color retention.

1) If the hair is damaged by repeated dyeing, the hair strength is reduced and elasticity is lost. 2) There is no problem of the above 1) and 2), such as hair thinning (hair color), and 2) the rash of the scalp is dyed and it is difficult to remove (hair manicure). It was found that hair cosmetics with good penetration and dyeing power can be provided. In other words, in the present invention, it has been found that, in addition to the color retention, safety is also provided.

Further, in the following, an embodiment of the hair color treatment method of the present invention will be described, but the present invention is not construed as being limited to the following embodiment.

Examples 6-8

First, a hair cosmetic applicable to the hair color treatment method of the present invention was prepared.

Regarding alkaline agents, ammonia water, ammonium carbonate, sodium carbonate, ethanolamines such as mono, di, or triethanolamine, ammonium hydrogen carbonate, arginine, and the like are considered. However, although ethanolamines such as monoethanolamine are non-volatile and have little odor, but they remain highly on the hair and may hurt the hair. Further, although arginine has a high affinity with hair, but it is weak as an action of an alkaline agent and has a mild reaction. Although aqueous ammonia (ammonia water) is the irritating odor due to volatile, but has a property that it has little residue on the hair and reacts quickly. Accordingly, in this embodiment, as the alkaline agent, as an example of ammonia water, it was tested with different concentrations.

In addition, about 80% of human hair is composed of keratin proteins derived from amino acid, L-cysteine is an amino acid that is also abundant in the hair. Therefore, L-cysteine and its salts were tried for the purpose of keeping the hair moisturized and flexible. Typical basic amino acids include L-arginine, L-lysine and L-histidine, but these are known to flow out when damaged, and there was found that 0.01 to 0.5% by mass of basic amino acids and salts thereof are preferable.

Table 6 shows the components of an example of the hair cosmetic composition in one embodiment of the present invention.

TABLE 6

| | | Examples | | |
|---|---|---|---|---|
| | Components | 6 | 7 | 8 |
| Alkaline agent | 25% Ammonia water | 1.00 | 2.00 | 3.00 |
| Amino acid group | L-Cysteine hydrochloride | 1.00 | 1.00 | 1.00 |
| | L-Arginine | 0.10 | 0.10 | 0.10 |
| | L-Lysine hydrochloride | 0.02 | 0.02 | 0.02 |
| | L-Histidine hydrochloride | 0.02 | 0.02 | 0.02 |

TABLE 6-continued

| | | Examples | | |
|---|---|---|---|---|
| | Components | 6 | 7 | 8 |
| Higher alcohol | Cetyl alcohol | 1.92 | 1.92 | 1.92 |
| | Lauryl alcohol | 0.24 | 0.24 | 0.24 |
| Common ingredients | Polyoxyethylene oleyl ether | 0.39 | 0.39 | 0.39 |
| | Polyoxyethylene lauryl ether | 0.27 | 0.27 | 0.27 |
| | Sodium lauryl sulfate | 0.18 | 0.18 | 0.18 |
| | Concentrated glycerin | 1.00 | 1.00 | 1.00 |
| | Hydrolyzed silk | 0.50 | 0.50 | 0.50 |
| | Cetyltrimethyl-ammonium chloride | 1.50 | 1.50 | 1.50 |
| | Fragrance | 0.20 | 0.20 | 0.20 |
| | Purified water | Residue | Residue | Residue |
| | Total (% by mass) | 100.00 | 100.00 | 100.00 |
| | pH | 8.72 | 9.60 | 10.38 |

TABLE 7

| | | | Examples | | |
|---|---|---|---|---|---|
| | | Components | 6 | 7 | 8 |
| A phase | | Purified water | Residue | Residue | Residue |
| | Alkaline agent | 25% Ammonia water | 1.00 | 2.00 | 3.00 |
| | Amino acid group | L-Cysteine hydrochloride | 1.00 | 1.00 | 1.00 |
| | | L-Arginine | 0.10 | 0.10 | 0.10 |
| | | L-Lysine hydrochloride | 0.02 | 0.02 | 0.02 |
| | | L-Histidine hydrochloride | 0.02 | 0.02 | 0.02 |
| B phase | Common ingredients | Concentrated glycerin | 1.00 | 1.00 | 1.00 |
| | | Hydrolyzed silk | 0.50 | 0.50 | 0.50 |
| | | Cetyltrimethyl-ammonium chloride | 1.50 | 1.50 | 1.50 |
| | | Fragrance | 0.20 | 0.20 | 0.20 |
| C phase | Emulsifying stability and viscosity-imparting ingredients | Cetyl alcohol | 1.92 | 1 92 | 1.92 |
| | | Lauryl alcohol | 0.24 | 0.24 | 0.24 |
| | | Polyoxyethylene oleyl ether | 0.39 | 0.39 | 0.39 |
| | | Polyoxyethylene lauryl ether | 0.27 | 0.27 | 0.27 |
| | | Sodium lauryl sulfate | 0.18 | 0.18 | 0.18 |
| | | Total (% by mass) | 100.00 | 100.00 | 100.00 |
| | | pH | 8.72 | 9.60 | 10.38 |

Table 7 shows an example of a method for preparing a hair cosmetic composition according to an embodiment of the present invention. The preparation method is as follows.

Preparation Method:
1. After confirming the dissolution of the amino acid group in the purified water of Phase A in Table 7, the alkaline agent is mixed uniformly. 2. Next, while stirring the A phase of Table 7, the B phase of Table 7 is added and mixed uniformly. 3. Add Phase C in Table 7 with moderate stirring and stir until uniform.

Moreover, the following models and electrodes were used for pH measurement.
Model of pH meter: F-52 (Horiba, Ltd.)
pH meter electrode: Type 9611 (Horiba, Ltd.)
In addition, Table 8 shows details of each component which is used.

TABLE 8

| | Components | Abbreviation or Product name | Manufacturer |
|---|---|---|---|
| Alkaline agent | Purified water 25% Ammonia water | Reagent grade 25% Ammonia water | Daiseikakou Co., Ltd. |
| Amino acid group | L-Cysteine hydrochloride | CSKE-200 | Osaka Sasaki Chemical Co., Ltd. |
| | L-Arginine | L-Arginine | Ajinomoto Co., |
| | L-Lysine hydrochloride | L-Lysine hydrochloride | Pure Chemical Co., Ltd. |
| | L-Histidine hydrochloride | L-Histidine hydrochloride | Tomo Chemical Co., Ltd. |
| Common ingredients | Concentrated glycerin | Concentrated glycerin for cosmetic | Sakamoto Pharmaceutical Co., Ltd. |
| | Hydrolyzed silk | SILK-1000 | Seiwa Kasei Co., |
| | Cetyltrimethyl-ammonium chloride | kohtamin 60W | Kao Corporation |
| | Fragrance | — | Kotobuki Fragrance Co., Ltd. |
| Emulsifying stability and viscosity-imparting | Cetyl alcohol Lauryl alcohol Polyoxyethylene oleyl ether Polyoxyethylene lauryl ether Sodium lauryl sulfate | EMACOL VS | Sanei Chemical Co., Ltd. |

From the above results, the higher alcohol preferably has 12 to 22 carbon atoms and can be contained for imparting smoothness to the hair, improving the emulsion stability, and adjusting the viscosity. In addition, 25% aqueous ammonia (ammonia water) is preferably 1 to 3% by mass, but considering the feeling of use and speed of reaction, irritation to the hand, and the burden on the scalp, it was found that 2.0% by mass of 25% aqueous ammonia is optimal.

In addition, actually, pretreatment was performed using the hair cosmetic composition of the present invention. That is, if a hair cosmetic (basic cuticle swelling agent) containing the hair cosmetic composition of the present invention is applied and left before hair color treatment, it was found that the alkaline agent in the swelling agent makes the cuticle open, and arginine, histidine hydrochloride, and lysine hydrochloride blended in the swelling agent permeates into the hair and exhibit a hair repair effect.

Thus, in the present invention, when performing hair dye, compared with conventional hair color and hair manicure, in the conventional method, there are problems that 1) if the hair is damaged by repeated dyeing, the hair strength is reduced and elasticity is lost to thin a hair (In the case of hair color), 2) if the scalp rash occurs, the rash part will stain and be difficult to remove (in the case of hair manicure). However, in the present invention, there is no problem of the above 1) and 2), it was found that hair cosmetics with good penetration and dyeing power can be provided. In other words, in the present invention, it has also been found that safety is provided when used in combination with a hair color in addition to color retention.

Examples 9-10

Next, a hair coloring agent applicable to the present invention was prepared.

With regard to the alkali agent (pH adjusting agent), from the viewpoint of being weakly alkaline and difficult to cause skin irritation, in the example, a test was conducted using ammonium bicarbonate as an example.

In addition, about 80% of human hair is composed of amino acid-derived from keratin proteins, L-cysteine is an amino acid that is also abundant in the hair, and in order to keep the hair moisturized and flexible, L-cysteine and its salts were blended. Typical basic amino acids include L-arginine, L-lysine and L-histidine, but these are known to flow out when damaged, and there was found that 0.01 to 0.5% by mass of basic amino acids and salts thereof are preferable.

Table 9 shows components of an example hair coloring agent composition in one embodiment of the present invention.

TABLE 9

| Components | Display name | Example 9 | Example 10 |
|---|---|---|---|
| Water phase | Water | Residue | Residue |
| | Glycerin | 1.00 | 1.00 |
| | BG | 1.00 | 1.00 |
| | Pentylene glycol | 1.00 | 1.00 |
| | Hydroxyethyl cellulose | 0.25 | 0.25 |
| | Steartrimonium bromide | 1.50 | 1.50 |
| | Isopropanol | 1.00 | 1.00 |
| Oil phase | Myristyl alcohol | 5.00 | 5.00 |
| | Behenyl alcohol | 1.00 | 1.00 |
| | Ethylhexyl palmitate | 2.00 | 2.00 |
| | Cetyl palmitate | 1.00 | 1.00 |
| | Glycol stearate | 2.00 | 2.00 |
| | Shea fat | 1.00 | 1.00 |
| Alkaline agent | Ammonium hydrogen | 0.70 | 1.00 |
| Preservatives and refreshing ingredients | Phenoxyethanol | 0.60 | 0.60 |
| | Menthol | 0.10 | 0.10 |
| | Ethanol | 1.00 | 1.00 |
| Antiinflammatory component | Glycyrrhizic acid 2K | 0.10 | 0.10 |
| Pigment | Basic blue 99 | 0.30 | 0.30 |
| | Basic brown 16 | 0.50 | 0.50 |
| | HC blue 2 | 0.60 | 0.60 |
| | HC yellow 4 | 0.20 | 0.20 |
| | HC yellow 2 | 0.10 | 0.10 |

TABLE 9-continued

|  | Components Display name | Example 9 | Example 10 |
|---|---|---|---|
| Amino acid group | Arginine | 0.10 | 0.10 |
|  | Histidine HCl | 0.02 | 0.02 |
|  | Lysine HCl | 0.02 | 0.02 |
|  | Total (% by mass) | 100.00 | 100.00 |
|  | pH | 6.80 | 7.50 |

The preparation method is as follows.
Preparation Method:
1. The aqueous phase (water phase) of Table 9 is warmed to 75-77° C. with stirring.
2. The oil phase in Table 4 is stirred while heating to 77-79° C. to make it uniform.
3. The pigment is added to water phase heated to 75-77° C. to homogenize, the oil phase is add to the mixture to emulsify and stir until uniform.
4. The content is slowly cooled, and when the temperature of the content is 43° C. or lower, the preservative, the refreshing component, the antiinflammatory component, and the amino acid group are added and stirred until uniform, and then cooled to 32° C. or lower.

Moreover, the following models and electrodes were used for pH measurement.
Model of pH meter: F-52 (Horiba, Ltd.)
pH meter electrode: Type 9611 (Horiba, Ltd.)

In addition, Table 10 shows details of each component which is used for the test.
Table 10 shows details of each component used.

In addition, a hair colorant containing the hair colorant composition of the present invention was actually prepared, and a color fading test was performed on the hair bundle. As a result, it was found that the hair coloring agent of the present invention was extremely excellent in color fading.

Conventionally, when a "hair color treatment" that does not contain paraphenylenediamine is applied and left as it is, although, the base color of this color treatment is a basic dye and HC dye, which are considered to be safer than oxidative dyes, since it was dyed on the hair, the color persistence after the hair dyeing was bad, and there was the fault that it was easy to lose color due to repeated shampooing. However, from the above results, it was found that not only the base color easily penetrates but also it can be applied from the new part to the hair tip without worrying about adhesion to the scalp because it does not contain an acidic dye.

Thus, in the present invention, when performing hair dye, compared with conventional hair color and hair manicure, in the conventional method, there are problems that 1) if the hair is damaged by repeated dyeing, the hair strength is reduced and elasticity is lost to thin a hair (In the case of hair color), 2) if the scalp rash occurs, the rash part will stain and be difficult to remove (in the case of hair manicure). However, in the present invention, there is no problem of the above 1) and 2), it was found that hair cosmetics with good penetration and dyeing power can be provided. In other words, in the present invention, it has also been found that safety is provided in addition to color retention.

TABLE 10

|  | Components Display name | Abbreviation or Product name | Manufacturer |
|---|---|---|---|
| Water phase | Water |  |  |
|  | Glycerin | Concentrated glycerin for cosmetic | Sakamoto Pharmaceutical Co., Ltd. |
|  | BG | 1,3-butylene glycol-P | KH Neochem Co., Ltd. |
|  | Pentylene glycol |  |  |
|  | Hydroxyethyl cellulose |  |  |
|  | Steartrimonium bromide | Catinal STB 70 | Toho Chemical Industry Co., |
|  | Isopropanol |  |  |
| Oil phase | Myristyl alcohol | KALCOL 4098 | Kao Corporation |
|  | Behenyl alcohol | Lanette 22 | BASF Japan Co., Ltd. |
|  | Ethylhexyl palmitate | Cegesoft C24 | BASF Japan Co., Ltd. |
|  | Cetyl palmitate | Cutina CP | BASF Japan Co., Ltd. |
|  | Glycol stearate |  |  |
|  | Shea fat | Refined shea butter | Koei Kogyo Co., Ltd. |
| pH adjuster (Alkaline agent) | Ammonium hydrogen carbonate |  |  |
| Preservatives and refreshing ingredients | Phenoxyethanol | Hisolve EPH | Toho Chemical Industry Co., Ltd. |
|  | Menthol | L-Menthol | K. Kobayashi & Co., Ltd. |
|  | Ethanol | Dehydrated ethanol | Kenei Pharmaceutical Co., Ltd. |
| Antiinflammatory component | Glycyrrhizic acid 2K | Dipotassium glycyrrhizinate | Maruzen Pharmaceutical Co., Ltd. |
| Pigment | Basic blue 99 |  |  |
|  | Basic brown 16 |  |  |
|  | HC blue 2 |  |  |
|  | HC yellow 4 |  |  |
|  | HC yellow 2 |  |  |
| Amino acid group | Arginine | L-Arginine | Kyowa Hakko Bio Co., Ltd. |
|  | Histidine HCl | L-histidine hydrochloride monohydrate | Wako Pure Chemical Industries, Ltd. |
|  | Lysine HCl | L-lysine hydrochloride | Wako Pure Chemical Industries, Ltd. |

Examples 11 to 16

Next, hair color treatment was performed using a hair cosmetic and a hair coloring agent.

Example 11

The hair is washed with "NanoSuppli Cleansing Shampoo GA" on a shampoo stand to wipe it off with a dry towel. By using 80 g of "Hair Cosmetic Composition (shown in Table 6 as mentioned below)" with a brush to apply the hair cosmetic composition to a new part (for white hair, it is easy to understand the effect of application because it is not dyed.), and to leave for 1 minute. Thereafter, it is washed with water and wiped off with a dry towel. 120 g of "hair coloring agent composition (shown in Table 6)" is applied with a brush around the new part and left to stand for 20 minutes. After that, "Ami-ion" is sprayed (alkaline treatment) for 6 minutes using a fog generator (the aim of the spray of "Ami-ion" is to increase color penetration). After applying the cuticle tightening agent, the hair color composition etc., is rinsed away with the shampoo "Apurucell Shampoo Premium" without leaving it, the hair treatment "Apurucell Treatment Premium" is blended well with hair, and then is rinsed. After that, the hair is dried and finished by using a hair dryer.

Example 12

The "Ami-ion" of the alkaline treatment is applied and wetted without shampooing it (it is easy to penetrate the hair cosmetic composition by wetting with alkaline). 80 g of "hair cosmetic composition" is applied to the new part using a brush and leave it for 5 minutes. After that, the hair is washed with water and dried with a hair dryer (to remove excess water so that the color treatment can be easily adsorbed to the hair). 120 g of "hair coloring agent composition" is applied so as not to be smeared with a brush around the new part, and is wrapped from above so that the hair coloring agent composition does not dry. The hair is warmed for 5 minutes using a hair dryer (to promote penetration and reaction), then let stand for 15 minutes. A cuticle tightening agent is applied, after that it is allowed for 5 minutes. The hair colorant composition is rinsed away with "Appulecel Shampoo Premium", and the hair is familiarized with the acidic rinse "Acid Amino Ion Water P" to familiarize with "Appulecel Treatment Premium", and then to rinse and to dry using a hair dryer.

Example 13

The "Ami-ion" of the alkaline treatment is applied and wetted without shampooing it (it is easy to penetrate the hair cosmetic composition by wetting with alkaline). 80 g of "hair cosmetic composition" is applied to the new part using a brush and leave it for 5 to 8 minutes. "Ami-ion" is sprayed (alkaline treatment) for 6 minutes using a fog generator (the aim of the spray of "Ami-ion" is to increase color penetration). After that, the hair is washed with water and dried with a hair dryer (to remove excess water so that the color treatment can be easily adsorbed to the hair). 120 g of "hair coloring agent composition" is applied so as not to be smeared with a brush around the new part, and is wrapped from above so that the hair coloring agent composition does not dry. The hair is warmed for 5 minutes using a hair dryer (to promote penetration and reaction), then let stand for 15 minutes. A cuticle tightening agent is applied, after that it is allowed to knead and familiarize with it and to the hair for 3 minutes. The hair colorant composition etc., is rinsed away with "Appulecel Shampoo Premium", and the hair is familiarized with "Appulecel Treatment Premium", and then to rinse and to dry using a hair dryer.

Example 14

80 g of "hair cosmetic composition" is applied to the new part using a brush, and "Ami-ion" is sprayed (alkaline treatment) for 6 minutes using a fog generator. The hair is washed with water and dried with a hair dryer. 120 g of "hair coloring agent composition" is applied so as not to be smeared with a brush around the new part, and is wrapped from above so that the hair coloring agent composition does not dry. The hair is warmed for 5 minutes using a hair dryer (to promote penetration and reaction), and "Ami-ion" is sprayed (alkaline treatment) for 6 minutes using a fog generator (the aim of the spray of "Ami-ion" is to increase color penetration). A cuticle tightening agent is applied, after that it is allowed to knead and familiarize with it and to the hair for 3 minutes. The hair colorant composition etc., is rinsed away with shampoo so called, "Appulecel Shampoo Premium", and the hair is familiarized with hair treatment so called, "Appulecel Treatment Premium", and then to rinse and to dry using a hair dryer.

Example 15

80 g of "hair cosmetic composition" is applied to the new part using a brush and leave it for 5 minutes. The hair is washed with water and dried with a hair dryer. 120 g of "hair coloring agent composition" is applied so as not to be smeared with a brush around the new part, and is wrapped from above so that the hair coloring agent composition does not dry. The hair is warmed for 5 minutes using a hair dryer (to promote penetration and reaction), then let stand for 6 minutes. "Ami-ion" is sprayed (alkaline treatment) for 6 minutes using a fog generator (the aim of the spray of "Ami-ion" is to increase color penetration). A cuticle tightening agent is applied, after that it is allowed to knead and familiarize with it and to the hair for 3 minutes. "Amino Film Conc Treatment a", a weakly alkaline treatment and "CH Hair Pack S", a film-forming treatment, are applied to improve the finish. The hair coloring composition etc., are rinsed with "Apurucell Shampoo Premium", and then the hair is familiarized with "Apurucell Treatment Premium" to rinse it, and then the hair is dried with a hair dryer. As a result, it is found that the application of the weakly alkaline treatment "Amino Film Conc Treatment a" and the film-forming treatment "CH Hair Pack S" cause the "hair color composition" to fade, resulting in a decrease in dyeing and color durability.

Example 16

The hair is washed with a shampoo "Bright hair painter shampoo" on a shampoo stand to wipe it off with a dry towel. By using 80 g of the hair cosmetic composition with a brush to apply the hair cosmetic composition to a new part, and to leave for 5 to 8 minutes. Thereafter, it is washed with water and dried with a hair dryer. 120 g of "hair coloring agent composition" is applied so as not to be smeared with a brush around the new part, and is wrapped from above so that the hair coloring agent composition does not dry. The hair is warmed for 5 minutes using a hair dryer (to promote penetration and reaction), then let stand for 6 minutes. "Ami-ion" is sprayed (alkaline treatment) for 9 minutes using a fog generator (the aim of the spray of "Ami-ion" is to increase penetration of the hair coloring agent). A cuticle tightening agent is applied, after that it is allowed to knead and familiarize with it and to the hair for 3 minutes. The hair colorant composition etc., is rinsed away with shampoo so called, "Appulecel Shampoo Premium", and the hair is familiarized with hair treatment so called, "Appulecel Treatment Premium", and then to rinse and to dry using a hair dryer.

The results are shown in Table 11. As the "hair cosmetic composition" shown in Table 11, the composition of Example 7 shown in Table 6 was used, and 80 g centered on the new part per person was used. Further, as the "hair coloring agent composition", the composition of Example 10 in Table 9 was used, and about 120 to 150 g per person was used (the amount used varies depending on the length of the hair).

In addition, Table 12 shows the component list of the cuticle tightening agent used (details of a component, a composition, a compounding quantity, etc.).

TABLE 12

| Abbreviation or Product name | Components | Manufacturer |
| --- | --- | --- |
| Sodium bromate | Sodium bromate | Kanto Chemical Co., Ltd. |
| L-glutamic acid for cosmetics | L-glutamic acid | Ajinomoto Co., Inc. |
| Citric acid | Citric acid | Showa Kako Co., Ltd. |
| QUARTAMIN 24P | Lauryltrimethylammonium chloride solution | Kao Corporation |
| Genagen CAB818J | Palm oil fatty acid amidopropyl betaine solution | Clariant Japan Co., Ltd. |

TABLE 11

|  | Example 11 | Example 12 | Example 13 | Example 14 | Example 15 | Example 16 |
| --- | --- | --- | --- | --- | --- | --- |
| Shampoo | ○*1 | — | — | — | — | ○*2 |
| Wetting the hair root | — | ○*3 | ○*3 | — | — | — |
| Application of hair cosmetic composition | ○*4 | ○*4 | ○*4 | ○*4 | ○*4 | ○*4 |
| Standing time | 1 minute | 5 minute | 5~8 minutes*5 | — | 5 minute | 5~8 minutes*5 |
| Spray using fog generator | — | — | 6 minutes*3 | 6 minutes*3 | — | — |
| Flushing | ○ | ○ | ○ | ○ | ○ | ○ |
| Drying | Wipe with a dry towel | Dry with a dryer | Dry with a dryer | Dry with a dryer | Dry with a dryer | Dry with a dryer |
| Application of hair color composition | ○*6 | ○*6 | ○*6 | ○*6 | ○*6 | ○*6 |
| Standing time | Natural standing for 20 minutes | Dryer for 5 minutes, natural standing for 15 minutes | Dryer for 5 minutes, natural standing for 15 minutes | Dryer for 5 minutes | Dryer for 5 minutes, natural standing for 6 minutes | Dryer for 5 minutes, natural standing for 6 minutes |
| Spray using fog generator | 6 minute | — | — | 6 minute | 6 minute | 9 minute |
| Cuticle tightening agent | ○*7 | ○*7 | ○*7 | ○*7 | ○*7 | ○*7 *13 |
| Tightening agent blending time | | Natural standing for 5 minutes | Familiarize for 3 minutes | Familiarize for 3 minutes | Familiarize for 3 minutes | Familiarize for 3 minutes |
| Weak alkaline treatment | — | — | — | — | ○*8 | — |
| Film formation treatment | — | — | — | — | ○*9 | — |
| Shampoo | ○*10 | ○*10 | ○*10 | ○*10 | ○*10 | ○*10 |
| Acid rinse | — | ○*11 | — | — | — | — |
| Hair treatment | ○*12 | ○*12 | ○*12 | ○*12 | ○*12 | ○*12 |
| Finishing process | ○ | ○ | ○ | ○ | ○ | ○ |
| Dyeing property | Δ | Δ | ○ | ○ | X | ◎ |
| Color persistence | X | Δ | ○ | ○ | X | ◎ |

In Table 11, for the evaluation of dyeability, ◎: good dyeability, ○: almost good dyeability, Δ: slightly bad dyeability, X: poor dyeability, And Regarding the evaluation of the color persistence, ◎: the color persistence is good, ○: the color persistence is almost good, Δ: the color persistence is slightly bad, X: the color persistence is bad. Moreover, in the examples of Examples 6 and 15, dyeing properties and color sustainability were improved by changing conditions such as the use of spray.

In addition, "*" in Table 11 is as follows.

*1 NanoSuppliment Cleansing Shampoo GA (Shampoo, Manufacturer/Seller: Sunny Place Co., Ltd.)

*2 Bright hair painter shampoo (Shampoo, Manufacturer and distributor: Sunny place shampoo)

*3 Ami-ion (Alkaline treatment, Manufacturer and distributor: Sunny Place Co., Ltd.)

*4 Hair cosmetic composition (basic cuticle swelling agent)

*5 (5 minutes for non-healthy hair, 8 minutes for healthy hair)

*6 Hair coloring agent composition (hair color treatment)

*7 Formulated with 8% sodium bromate. (Refer to component details, composition and amount)

*8 Amino Film Conc Treatment a (Slightly alkaline treatment, Distributor: Sunny Place Co., Ltd.)

*9 CH Hair Pack S (Film formation treatment, Distributor: Sunny Place Co., Ltd.)

*10 Apurucell Shampoo Premium (Shampoo, Manufacturer and distributor: Sunny Place Co., Ltd.)

*11 Acidic Amino Ion Water P (Acid Rinse, Distributor: Sunny Place)

*12 Apurucell Treatment Premium (Hair Treatment, Manufacturer/Seller: Sunny Place Co., Ltd.)

TABLE 12-continued

|  |  | Components | Blending amount |
|---|---|---|---|
| A phase |  | Purified water | Residue |
|  | Oxidant | Sodium bromate | 8.00 |
|  | Acidic amino acids | L-glutamic acid | 0.01 |
|  | pH adjuster | Citric acid | Appropriate amount |
| B phase | Cationic surfactant | Lauryltrimethylammonium chloride solution | 0.27 |
| C phase | Amphoteric surfactant | Palm oil fatty acid amido-propyl betaine solution | 0.58 |
|  |  | Total (% by mass) | 100.00 |
|  |  | pH | 5.40 |

Also, the method for adjusting the cuticle tightening agent is as follows. Adjustment method:
1. The remaining ingredients are mixed evenly with the purified water of Phase A in Table 12.
2. While stirring the A phase of Table 12, add the B phase of Table 12 and mix uniformly.
3. Phase C in Table 12 with moderate stirring is added to the mixture to stir until uniform.
4. In order to adjust to an isoelectric band (pH 4.5 to 5.5) of the hair, the pH of the preparation is adjusted to around pH 5.40 using citric acid.

The following models and electrodes were used for pH measurement.
Model of pH meter: F-52 (Horiba, Ltd.)
pH meter electrode: Type 9611 (Horiba, Ltd.)

As a result, among Examples 11 to 16, the result of Example 16 was the best under these conditions. As a possible reason, it can be mentioned that the hair cosmetic composition (basic cuticle swelling agent) can adsorbed by removing the inhibiting factors such as hair styling and sebum etc., to penetrate inside by using an alkaline shampoo having a pH of 10.24. It was also found that the hair color treatment that remained by washing while opening the cuticle leaked out, and it was possible to prevent it from becoming darker and darker when the number of treatments was repeated (preventing overlapping color dyeings). It was also found that after washing the hair cosmetic composition (basic cuticle swelling agent) with water, by drying with a dryer rather than towel drying, it is possible to prevent the hair color composition from thinning due to the residual of the excess moisture. Further, it has also been found that the hair coloring composition is washed with water and then a cuticle tightening agent is applied to efficiently enhance color dyeing and color persistence.

Moreover, as a result of a patch test of the above-mentioned hair cosmetics and hair coloring agents, the skin irritation index was 0.0 to 2.5 for 20 subjects, and both were confirmed to be safe products.

INDUSTRIAL APPLICABILITY

According to the present invention, it is possible to improve the color tone with respect to the hair color processing which was not good in color, and the industrial utility value is high in a wide range.

The invention claimed is:

1. A hair color treatment method comprising:
   a step of applying a hair cosmetic comprising an alkaline agent, a first amino acid, a higher alcohol having 12 to 22 carbon atoms, a surfactant, and a thickener; and
   after applying the hair cosmetic, a step of applying a hair coloring agent comprising a basic dye, an HC dye, a second amino acid, a first cationic surfactant, a thickener, an oil agent, a first pH adjusting agent, and a wetting agent, wherein the hair coloring agent has a pH of 6.8 or more.

2. A hair color treatment method of claim 1, wherein the method further comprises a step of applying a cuticle tightening agent including at least one selected from sodium bromate and hydrogen peroxide, a second cationic surfactant, and a second pH adjusting agent, after applying the hair coloring agent.

3. A hair color treatment method according to claim 1, wherein when the hair cosmetic is applied, an exposure time is 5 to 20 minutes.

4. A hair color treatment method according to claim 1, wherein when the hair coloring agent is applied, an exposure time is 5 to 15 minutes after warming for 1 to 10 minutes by use of a hair dryer.

5. A hair color treatment method according to claim 1, wherein the alkaline agent is at least one selected from ammonia water, ammonium carbonate, sodium carbonate, ethanolamines, ammonium hydrogen carbonate, and arginine.

6. A hair color treatment method according to claim 1, wherein the first or second amino acid is at least one selected from cysteine, arginine, lysine, and histidine.

* * * * *